US005383916A

United States Patent [19]
Brown

[11] Patent Number: 5,383,916
[45] Date of Patent: Jan. 24, 1995

[54] SUPPORT MEMBER FOR A TANNING BED OR COMPARABLE DEVICE

[75] Inventor: Roger A. Brown, Dallas, Tex.

[73] Assignee: Puretan International, Inc., Dallas, Tex.

[21] Appl. No.: 982,014

[22] Filed: Nov. 24, 1992

Related U.S. Application Data

[63] Continuation of Ser. No. 789,868, Nov. 12, 1991, abandoned.

[51] Int. Cl.6 ............................................. A61N 5/06
[52] U.S. Cl. ........................................ 607/91; 607/94
[58] Field of Search ................... 607/91, 44, 88, 89, 607/90; 128/376, 396; 250/504 R; 362/84, 85, 130, 134, 221, 226, 411; 361/395, 384, 391

[56] References Cited

U.S. PATENT DOCUMENTS

| 1,664,992 | 4/1928 | Pongo . | |
|---|---|---|---|
| 2,148,174 | 2/1939 | Rold . | |
| 4,399,487 | 8/1983 | Neumann | 361/395 |
| 4,401,351 | 8/1983 | Record | 361/395 |
| 4,412,112 | 10/1983 | Ishikawa | 361/391 |
| 4,660,561 | 4/1987 | Nielsen . | |
| 4,683,887 | 8/1987 | Kramer et al. . | |
| 4,683,888 | 8/1987 | Kramer et al. | 128/376 |
| 4,729,375 | 3/1988 | Jegers et al. | 128/376 |
| 4,881,548 | 11/1989 | Kramer . | |
| 4,918,319 | 4/1990 | Kruithof . | |

FOREIGN PATENT DOCUMENTS

| 3413662 | 10/1985 | Germany | 128/396 |
|---|---|---|---|
| 3627106 | 2/1988 | Germany | 128/396 |
| 3708821 | 9/1988 | Germany | 128/395 |
| 3708872 | 9/1988 | Germany | 128/395 |

Primary Examiner—Mark S. Graham
Attorney, Agent, or Firm—Richards, Medlock & Andrews

[57] ABSTRACT

A support member for tanning beds or comparable devices is designed to have the various electrical components used in operating the tanning bed, or comparable device, on a removable cassette that can be readily removed and sent to be serviced independent of the tanning bed or comparable device. The support member comprises a housing which defines an open compartment in which the cassette is slidably disposed. The cassette has a rack for carrying the various electrical components attached to a front panel which closes over the compartment.

25 Claims, 2 Drawing Sheets

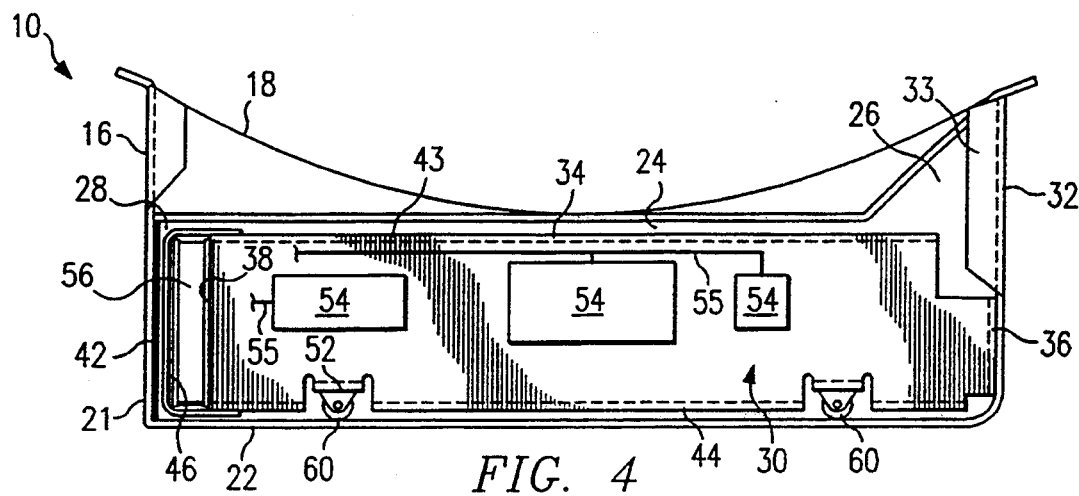

SUPPORT MEMBER FOR A TANNING BED OR COMPARABLE DEVICE

This is a continuation of application Ser. No. 07/789,868, filed Nov. 12, 1991, now abandoned.

TECHNICAL FIELD OF THE INVENTION

The present invention relates to a support member for a tanning bed or comparable device. In one aspect it relates to such a support member that houses the various electrical components used in the operation of the tanning bed or comparable device.

BACKGROUND OF THE INVENTION

Tanning beds are typically constructed so as to have a large heavy bed with a separate upper panel which is raised and lowered over a person laying on the bed. Both the bed and upper panel contain a plurality of ultraviolet lights and typically various electrical components including circuits, switches and basic elements required to control and operate the tanning bed. When the various electrical components are built into the bed or upper panel, serviceability of such components is greatly reduced because either qualified repair personnel must be called to the site of the tanning bed or the tanning bed must be sent to the qualified repair personnel. Extensive labor and cost is involved in shipping a tanning bed, or in paying for qualified repair personnel to travel to the site of the tanning bed.

One attempt to improve the serviceability of the tanning bed components is to confine all the components to a single box which is then connected to the bed and upper panel through various wire connections. When the components fail or otherwise need servicing, the box can be disconnected from the wires and sent in for servicing. The drawback of such a box is that they generate large amounts of heat and are generally placed underneath the tanning bed which increases the heat under the tanning bed and discomfort to the person using the tanning bed. Also such boxes take up space under the tanning bed and a tanning bed with such a box is not as aesthetically pleasing as a tanning bed that has its components inside the bed or upper unit. Also, a separate box constitutes a separate item that must be moved every time the tanning bed is moved.

Thus a need exists for a way to permit the ready servicing of the electrical components used in operating a tanning bed and at the same time eliminate the need for a separate, free-standing box of components.

SUMMARY OF THE INVENTION

The present invention provides a support member for supporting a treatment table, such as a tanning bed, and housing various electrical components used in conjunction with the treatment table. In a specific embodiment of the invention, the support member comprises a housing which supports a tanning bed and has a top side dimensioned to hold the tanning bed. The housing defines a compartment. The support member further comprises a cassette which is slidably disposed in the compartment. The cassette is readily removable from the compartment without affecting the support strength of the tanning bed. The cassette comprises a front panel which closes over the compartment and a rack attached to the front panel and extended into the compartment. The rack is dimensioned for carrying various electrical components used in operation of the tanning bed. A further aspect of the present invention comprises a fan on the inside of the compartment which is oriented to draw air into the compartment and out one or more vents in the housing to transfer heat away from the various electrical components on the rack.

By housing various electrical components used in operation of the tanning bed in a support member, the present invention eliminates the need for a separate box containing electrical components. As a result, the amount of heat underneath the tanning bed is reduced, the aesthetic appearance of the tanning bed is improved, and an extra item that must be moved around with the tanning bed is eliminated.

The present invention allows for the various electrical components to be readily removed from the support member and shipped to qualified repair personnel. The housing is capable of supporting the tanning bed without the cassette, so removal of the cassette is as simple as pulling the cassette out of the support member. The tanning bed does not have to be moved. The design of the cassette of the present invention allows easy access to the components which further increases the serviceability of the components on the cassette.

BRIEF DESCRIPTION OF THE DRAWINGS

For a more complete understanding of the present invention and the advantages thereof, references is now made to the following Detailed Description of the invention taken in conjunction with the accompanying drawings, in which:

FIG. 4 is a side view of the preferred embodiment of the support member shown in FIG. 3 with a side panel removed to show the interior of the support member;

FIG. 5 is a rear view of the preferred embodiment of the support member shown in FIG. 3; and FIG. 6 is a perspective view of the preferred embodiment of the support member of the present invention with the cassette removed from the housing.

DETAILED DESCRIPTION

Figure 1:
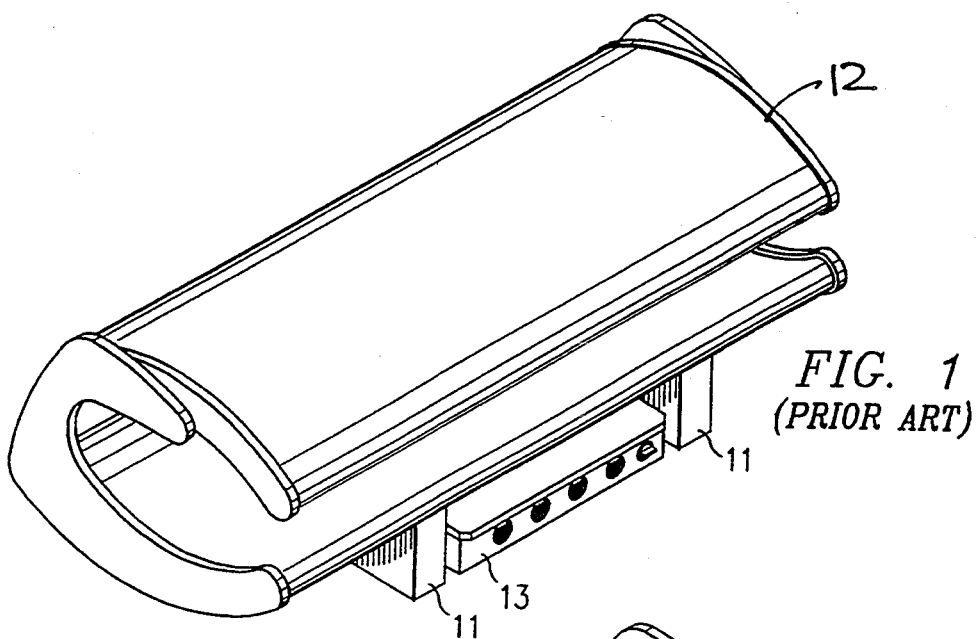
FIG. 1 is an isometric view of a prior art tanning bed with a separate, free-standing box containing the various electrical components.

FIG. 1 illustrates a prior art tanning bed 12 with separate box 13 which houses various electrical components used to operate the tanning bed. Conventional support members 11 support tanning bed 12. Conventional support members 11 are typically a sheet metal housing composed of various panels welded together. Box 13 generates heat which collects under tanning bed 12 and creates discomfort for a person using the tanning bed. Also, tanning bed 12 with box 13 is not as aesthetically pleasing as tanning bed 12 without box 13. Box 13 takes up space under the bed and is a separate item that must be moved every time the tanning bed is moved. While box 13 can be disconnected from the tanning bed and sent to be serviced, the box must be disassembled to access the components. The present invention provides a new and useful support member that eliminates box 13 by housing various electrical components out of view in the support member on a removable cassette that can be readily removed and sent to be serviced independent of the tanning bed.

Figure 2:
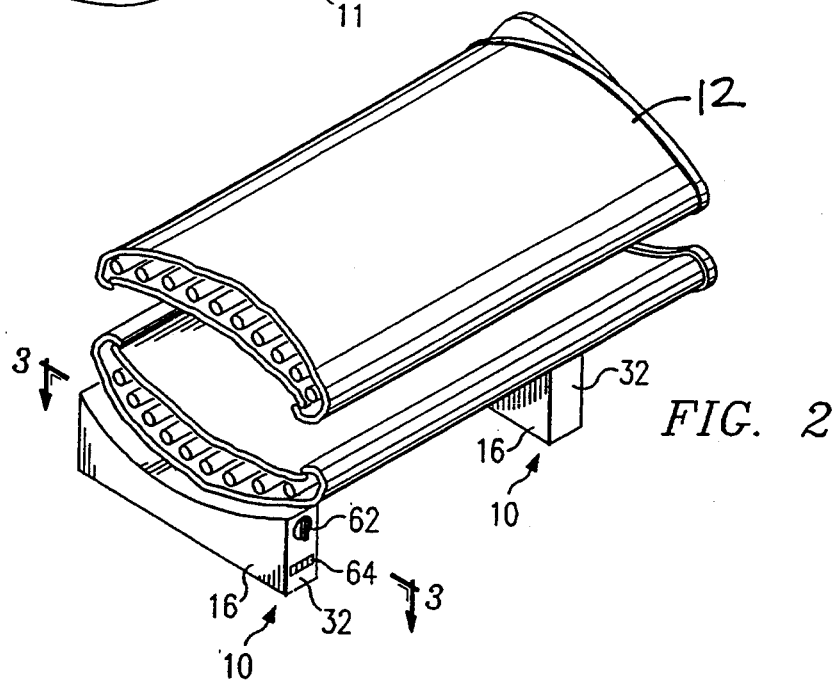
FIG. 2 is an isometric view of two support members of the present invention in use with a tanning bed with a portion of the tanning bed broken away to completely reveal one of the support members.
Figure 3:
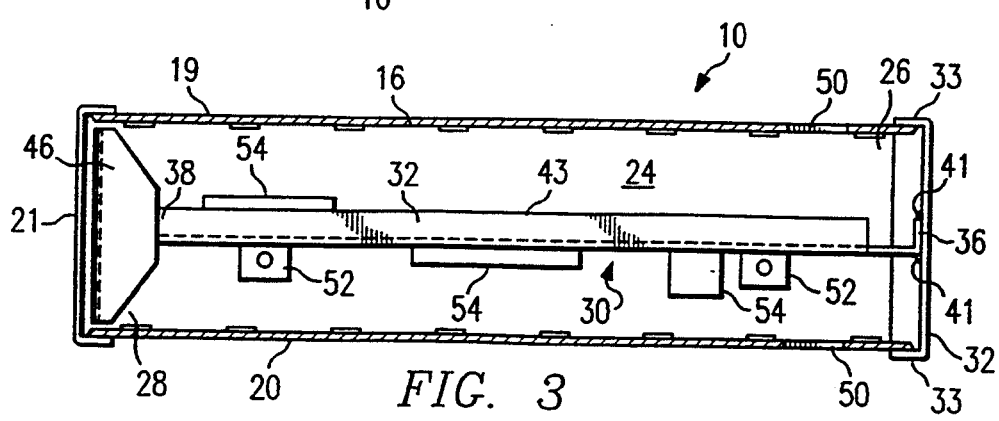
FIG. 3 is a horizontal sectional view taken along lines 3—3 of FIG. 2.

FIG. 2 illustrates two support members 10 of the present invention in place underneath tanning bed 12. The revealed support member contains timer knob 61 and hour meter 64. It can be seen that box 13 of FIG. 1 has been eliminated. A support member 10 comprises housing 16 with removable front panel 32. The various electrical components and switches that were previously housed either in a separate box or within the tanning bed itself are now conveniently housed in support members 10 on a rack attached to panel 32 inside housing 16.

With reference to FIGS. 3-6, the preferred embodiment of a support member 10 of the present invention will now be described in further detail. Support member 10 comprises housing 16 which, when used with another support member, is capable of supporting a tanning bed. Housing 16 has top side 18 dimensioned to receive and hold a tanning bed. Top side 18 is concave to receive a convex bottom of a tanning bed. Top side 18 can be any shape depending on the bottom of the tanning bed desired to be supported. Top side 18 is easily formed from various types of sheet metals.

Housing 16 defines compartment 24. In the preferred embodiment, housing 16 has first side panel 19, second side panel 20, back panel 21, and bottom panel 22 joined together and to top side 18 to form a generally rectangular box with a curved top. Compartment 24 has a front 26 which is open and a back 28 at back panel 21. The edges of the various panels are bent at right angles to fit flush with adjoining panels and then spot welded. Housing 16 by itself is capable of supporting a tanning bed.

Cassette 30 is slidably disposed in compartment 24 and readily removable from compartment 24 without affecting the support strength of the tanning bed. Cassette 30 has front panel 32 which closes over compartment 24. Side flanges 33 of front panel 32 grippingly slide over the ends of first side panel 19 and second side panel 20 when cassette 30 is completely inserted in compartment 24. Rack 34 has first end 36 attached to front panel 32 and second end 38 disposed at back 28 of compartment 24 proximate back panel 21. In a preferred embodiment, gasket 42 is disposed on the inside of back panel 21 to prevent rack 34 from contacting back panel 21 and causing noise due to vibrations. Rack 34 is made from sheet metal and has first end 36 bent at a right angle so as to provide a surface to mate with the inside front panel 32 and create edges 41 along which spot welds are placed to connect rack 34 to front panel 32. Rack 34 is bent along top 43 and bottom 44 to increase rigidity of rack 34.

Second end 38 of rack 34 has attached to it bracket 46. Bracket 46 is spot-welded to top 43 and bottom 44 at second end 38 of rack 34. Fan 56 is mounted between bracket 46 and second end 38. Fan 56 is oriented to draw air through intake vents 48 in bracket 46, move it across rack 34 and out outlet vents 50 located at front 26 of compartment 24 in housing 16. Back panel 21 has opening 40 which exposes intake vents 48 in bracket 46. Outlet vents 50 are preferably located in first side panel 19 and second side 20 towards front 26 of compartment 24; however, they can be located in front panel 32. Various electrical components 54 used in operation of the tanning bed are mounted to rack 34. Electrical leads 55 from components 54 are routed along rack 34 to the rear of the unit where they exit through hole 66 (FIG. 5) in bracket 46. Hole 66 is exposed through opening 40 in back panel 21 as shown in FIG. 5.

Rack 34 also has wheel flanges 52 which are cut out of bottom 44 and turned upward to be parallel with bottom panel 22. Rollers 60 are mounted to wheel flanges 52 to carry cassette 30 on bottom panel 22.

When it is desired to remove cassette 30, front panel 32 is grabbed at side flanges 33 extending around first side panel 19 and second side panel 20. On pulling front panel 32 at side flanges 33, cassette 30 will readily slide on rollers 60 along bottom panel 22. Slides may be used instead of rollers 60 as long as cassette 30 can be readily extracted from housing 16. Rack 34 is designed to extend down the middle of compartment 24 so that the electrical components are attached on the outside of rack 34 making them readily accessible for servicing or replacement.

When cassette 30 is ready to be returned to support member 10, bracket 46 and second end 38 are inserted into compartment 24 and cassette 30 readily slides by rollers 60 on bottom panel 22 until side flanges 33 of front panel 32 grippingly slide over first side panel 19 and second side panel 20 to retain cassette 30 in compartment 24. Retaining screws can be screwed through side flanges 33 into the side panels to further retain cassette 30 in compartment 24. Gasket 42 absorbs vibrations from fan 56 to reduce noise and prevent metal to metal contact between bracket 46 and back panel 21.

FIG. 6 shows front panel 32 with cutouts 58 which allow for placement of components such as timer knob 62 and hour meter 64 shown on the revealed support member in FIG. 2. When cassette 30 is in place, front panel 32 neatly closes over compartment 24 to give the appearance of a unitary, aesthetic support member. Only housing 16, front panel 32, and any components placed through front panel 32 are readily visible from the front. Alternatively, one support member can be sized to be able to house all the electrical components so that the other support member can be a conventional support member.

In an alternative embodiment, rack 34 can be attached to front panel 32 with screws or other fasteners. This would allow the removal of rack 34 from front panel 32 so that only rack 34 would need to be sent for servicing. Also in this alternative embodiment, front panel 32 can be replaced over compartment 24 while rack 34 is out for service.

It should be understood that the support member of the present invention can be used with devices other than tanning beds, for example, therapeutic beds, various hospital beds, work tables, machining benches, etc.

While a particular embodiment of the present invention has been shown and described, it will be obvious to those skilled in the art that changes and modifications may be made without departing from the invention and its broader aspects and, therefore, the aims of its appended claims are to cover all such changes and modifications as fall within the true spirit and scope of this invention.

What is claimed is:

1. A tanning bed assembly for placement on a surface comprising:
    a) a tanning bed;
    b) at least two support legs for supporting the tanning bed above the surface, each support leg having a top end for engagement with the underside of said bed at points spaced one from the other, and a second end for engagement with the surface, one of said support legs having a compartment therein; and c) a cassette adapted for holding electrical components used in conjunction with the tanning bed, said cassette being receivable in said compartment and removable from said compartment without affecting the support strength of the support leg for supporting the bed said compartment having at least one outlet vent adapted to facilitate dissipation of heat from the electrical components, out of said compartment and away from the tanning bed.

2. The bed assembly of claim 1 wherein said cassette comprises a front panel and a rack attached to said front panel that extends into said compartment.

3. The bed assembly of claim 2 wherein said compartment has at least one outlet vent to facilitate dissipation of heat therefrom.

4. The bed assembly of claim 3 further comprising a fan located in said compartment and oriented to move air into said compartment and out said at least one outlet vent to remove heat from said compartment and away from the tanning bed.

5. The bed assembly of claim 4 wherein said attached to said cassette.

6. The bed assembly of claim 4 wherein said compartment has at least one intake vent through which said fan can draw air into said compartment.

7. The bed assembly of claim 1 further comprising at least one roller attached to said cassette to facilitate removal of said cassette from said compartment.

8. The bed assembly of claim 2 wherein said compartment has an open front and a back, said rack has a first end connected to said front panel and a second end, and, when said cassette is in said compartment, said second end of said rack is at said back of said compartment, said front panel covers said front of said compartment, and said cassette can be removed from said compartment through said front of said compartment.

9. The bed assembly of claim 8 further comprising a bracket attached to said second end of said rack and a fan attached between said bracket and said second end, said bracket having at least one intake vent and said van oriented to draw air through said intake vent and out of said outlet vent to remove heat from said compartment and away from said tanning bed.

10. The bed assembly of claim 9 wherein, when said cassette is in said compartment, said compartment has an opening so as to expose said at least one intake vent to outside said compartment.

11. The bed assembly of claim 2 wherein said rack is designed for carrying electrical components such that the electrical components are readily accessible for servicing when said cassette is removed from said compartment.

12. The bed assembly of claim 2 wherein, when said cassette is in said compartment, only the outside of said compartment and the said front panel of said cassette are visible.

13. The bed assembly of claim 2 further comprising a plurality of electrical components used in operation of the tanning bed attached to said rack.

14. A tanning bed assembly for placement above a surface comprising:
a) a tanning bed;
b) at least two housings, with at least one of said housings for receiving electrical components used in conjunction with the bed, said housings extending between the floor surface and the tanning bed and in contact with the bed at points spaced one from the other such that the bed is supported over the surface by the housings; and
c) a cassette disposed in one of said housings and adapted for holding electrical components used in conjunction with the bed, said cassette removable from said one said housing without affecting the support strength of the one said housing and said one said housing and cassette defining an outlet for removal of heat from said housing and away from said tanning bed.

15. The bed assembly of claim 14 wherein said cassette comprises a front panel and a rack attached to said front panel that extends into one said housing.

16. The bed assembly of claim 15 wherein said one said housing has a compartment with an open front and a back, said rack has a first end connected to said front panel and a second end, and, when said cassette is in said one said housing, said second end of said rack is at said back of said compartment, said front panel covers said front of said compartment, and said cassette can be removed from said compartment through said front of said compartment.

17. The bed assembly of claim 16 further comprising a bracket attached to said second end of said rack and a fan attached between said bracket and said second end, said bracket having at least one intake vent and said fan oriented to draw air through said intake vent.

18. The bed assembly of claim 17 wherein, when said cassette is in said one said housing, said one said housing has an opening so as to expose said at least one intake vent to outside said one said housing.

19. The bed assembly of claim 15 wherein said rack is designed for carrying electrical components such that the electrical components are readily accessible for servicing when said cassette is removed from said one said housing.

20. A tanning bed assembly having electrical components used in conjunction therewith and for support over a surface comprising:
a) a tanning bed;
b) at least two housings, each having a top end and configured to engage the bed at points spaced one from the other and a bottom end configured to engage the surface, the top end having an area substantially equal to the area of the bottom end; and
c) a removable cassette disposed in one of said housing and adapted for holding electrical components used in conjunction with the tanning bed, said one said housing and cassette defining an outlet for the removal of heat from the one said housing and away from the tanning bed.

21. The bed assembly of claim 20 wherein said cassette comprises a front panel and a rack attached to said front panel that extends into said one said housing.

22. The bed assembly of claim 21 wherein said one said housing has a compartment with an open front and a back, said rack has a first end connected to said front panel and a second end, and, when said cassette is in said one said housing, said second end of said rack is at said back of said compartment, said front panel covers said front of said compartment, and said cassette can be removed from said compartment through said front of said compartment.

23. The bed assembly of claim 22 further comprising a bracket attached to said second end of said rack and a fan attached between said bracket and said second end, said bracket having at least one intake vent and said fan oriented to draw air through said intake vent.

24. The bed assembly of claim 23 wherein, when said cassette is in said one said housing, said one said housing has an opening so as to expose said at least one intake vent to outside said one said housing.

25. The bed assembly of claim 21 wherein said rack is designed for carrying electrical components such that the electrical components are readily accessible for servicing when said cassette is removed from said one said housing.

* * * * *